United States Patent [19]

Brumbach

[11] Patent Number: 5,486,162
[45] Date of Patent: Jan. 23, 1996

[54] BUBBLE CONTROL DEVICE FOR AN ULTRASONIC SURGICAL PROBE

[75] Inventor: Joseph F. Brumbach, Niles, Ill.

[73] Assignee: FibraSonics, Inc., Chicago, Ill.

[21] Appl. No.: 371,145

[22] Filed: Jan. 11, 1995

[51] Int. Cl.$^6$ ............................................. A61B 17/00
[52] U.S. Cl. ............................................................ 604/22
[58] Field of Search ...................... 128/660.03; 604/22; 606/169–171

[56] References Cited

U.S. PATENT DOCUMENTS

| | | | |
|---|---|---|---|
| 3,526,219 | 9/1970 | Balsmuth | 604/22 |
| 3,805,787 | 4/1974 | Banko | 604/22 |
| 3,945,375 | 3/1976 | Banko | 606/170 |
| 4,316,271 | 2/1982 | Evert | 128/662.03 |
| 4,320,761 | 3/1982 | Haddad | 606/107 |
| 4,344,777 | 8/1982 | Siposs | 55/178 |
| 4,417,578 | 11/1983 | Banko | 606/169 |
| 4,428,748 | 1/1984 | Peyman et al. | 604/22 |
| 4,515,583 | 5/1985 | Sorich | 604/22 |
| 4,681,561 | 7/1987 | Hood et al. | 604/22 |
| 4,741,731 | 5/1988 | Starck et al. | 604/22 |
| 4,816,017 | 3/1989 | Hood et al. | 604/22 |
| 4,816,018 | 3/1989 | Parisi | 604/22 |
| 4,983,160 | 1/1991 | Steppe et al. | 604/22 |
| 5,151,084 | 9/1992 | Khek | 604/22 |

*Primary Examiner*—Francis Jaworski
*Attorney, Agent, or Firm*—Welsh & Katz, Ltd.

[57] ABSTRACT

An improved bubble control device is provided for an ultrasonic surgical probe or tool having a needle and a sleeve surrounding and spaced from the needle for at least a portion of the length of the needle, the device comprising a cylindrical hollow body having a bore and adapted to be positioned in the annular passage between the needle and the sleeve with the needle being received in the bore of the body, and having at least one groove formed on its peripheral surface through which fluid supplied to the annular passage between the needle and the sleeve and containing cavitation bubbles formed upon contact of the fluid with vibrating components are restricted in their passage by being forced through the space between the at least one groove formed on the peripheral surface of the body and the sleeve, and through the space between the body and the needle, thereby reducing the passage of bubbles formed in the fluid.

18 Claims, 2 Drawing Sheets

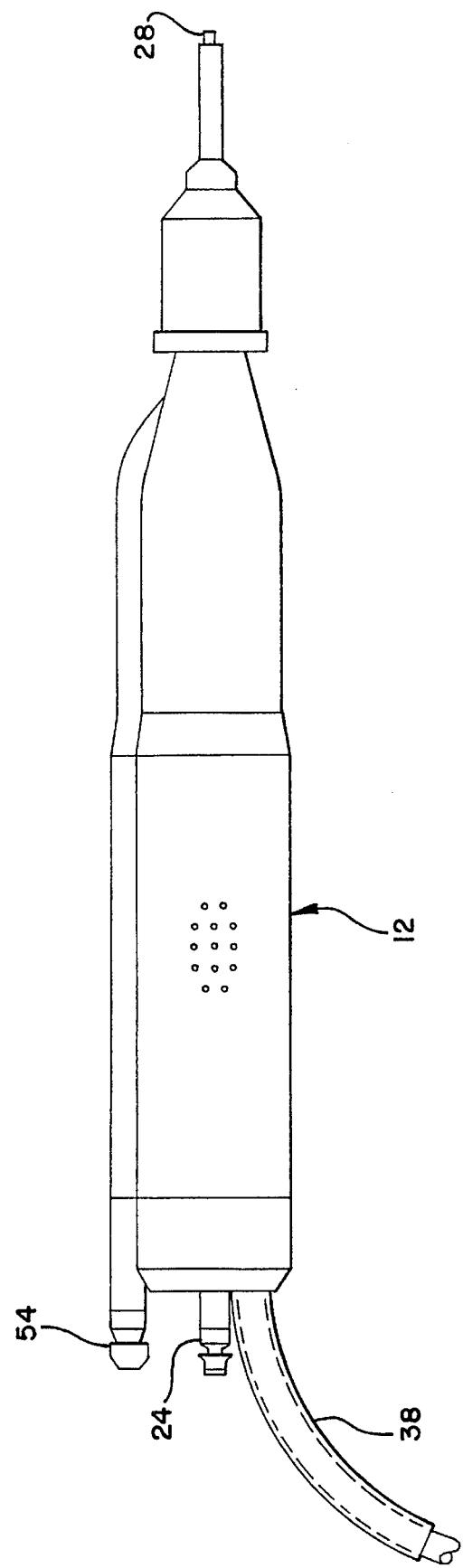

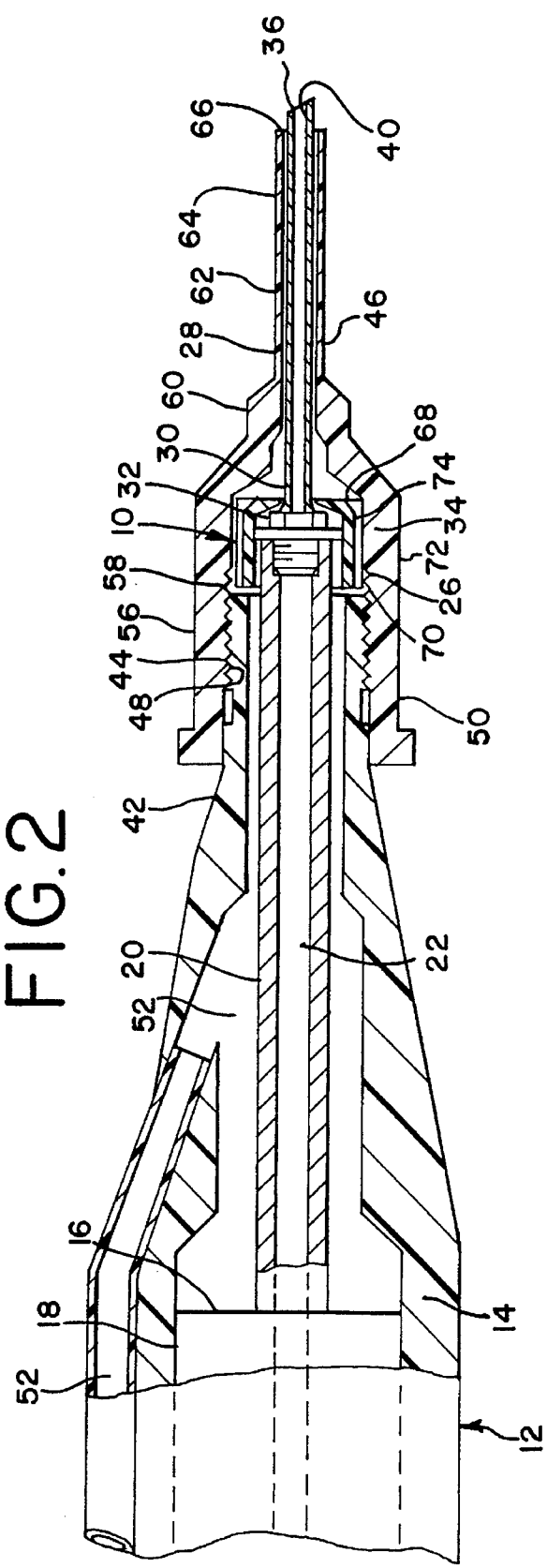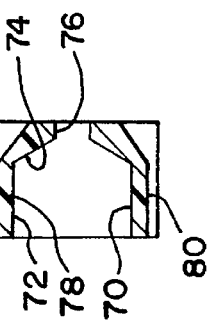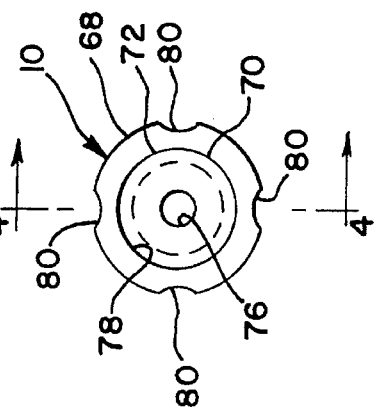

BUBBLE CONTROL DEVICE FOR AN ULTRASONIC SURGICAL PROBE

BACKGROUND OF THE INVENTION

1. Field of the Invention

The present invention relates to devices for ultrasonic surgical probes or scalpels for use in the removal of inorganic or organic tissue from a living body, and, more particularly, to a device adapted to be installed within an ultrasonic surgical tool capable of reducing the formation of bubbles imparting ultrasonic vibrations in the stream of irrigating or other fluid flowing to the operating needle of the tool.

2. Description of Related Art

Ultrasonic probes or scalpels for the fragmentation and removal of inorganic materials and fluids from living beings have been long known to the art. For example, U.S. Pat. No. 2,227,727, issued Jan. 7, 1941 to Vincent Leggiardro, discloses an apparatus having a two part housing, with a sonic transducer in one part and a reciprocating rod in another part, for fragmenting naturally formed stones, such as bladder stones, kidney stones, and the like. In later apparatus the transducer and probe were connected together to form a unitary instrument. For example, in U.S. Pat. No. 3,896,811, issued Jul. 29, 1975 to Karl Storz, the transducer and rod-like probe are coupled and both are enveloped by a jacket providing an air gap and preventing the sides of the probe from contacting the body except at its end.

An improvement in such instruments is disclosed in U.S. Pat. No. 3,990,452, issued Nov. 9, 1976 to Edward J. Murry and Joseph F. Brumbach, which also reviews a number of articles relating to the development of ultrasonics in medicine and, particularly for use in cataract surgery, and notes the incorporation of irrigation and aspiration with ultrasonics.

The use of irrigating fluid flowing to the needle in an ultrasonically vibrated surgical tool and flowing to the operating site is now widely used, particularly for ophthalmic surgery. However, the passage, of the irrigation fluid about the ultrasonically vibrating needle and connectors between the needle and the ultrasonic transducer, frequently causes the formation of cavitation bubbles in the stream of flowing irrigation fluid. These bubbles decrease the efficiency of the fluid where the fluid is utilized to cool the needle, and creates a visual obstruction to the surgeon at the operating site in delicate surgery where the irrigating fluid is directed to the operating site.

To reduce the formation or the passage of cavitation bubbles from the ultrasonically vibrating parts of the tool and particularly their passage to the operating site, various devices have been included in the tool. For example, the use of a circular diaphragm with openings positioned in the fluid path at a point prior to the fluid contacting the needle is disclosed in U.S. Pat. No. 4,428,748, issued Jan. 31, 1984 to Gholam A. Peyman, et. al. In two U.S. Pat. Nos. 4,681,561 and 4,816,017, issued Jul. 21, 1987, and Mar. 28, 1989, respectively, to Larry L. Hood and Maurice M. Imonti, a decoupling sleeve having a collar portion is placed in the irrigating fluid path about the ultrasonically vibrated tool or needle and by means of the collar is retained within the interior of a tip cap sleeve member, the sleeve impeding the transmission of ultrasonic energy through the fluid as the fluid passes through the sleeve. In another U.S. Pat. No. 5,151,084, issued Sep. 29, 1992, to Sokhuom Khek, a disk-shaped baffle with holes is positioned in the fluid path about the needle after contact with the ultrasonic motor and the connectors between the motor and the needle to reduce bubbles in the fluid as the fluid passes through the baffle and to improve the visibility at the operating site.

However, none of these arrangements are completely satisfactory to reduce the presence of bubbles in the irrigating fluid supplied to the needle, to cool the latter, and to the operating site. Therefore, there is a need for an improved ultrasonic surgical tool construction which provides for improved reduction in the amount of bubbles in the irrigating fluid supplied to the needle and exiting from the fluid passage surrounding the needle to the surgical site.

SUMMARY OF THE INVENTION

Hence, it is one object of the present invention to provide an improved bubble control device for an ultrasonic surgical probe.

It is another object of the present invention to provide an improved device to be positioned in the irrigating fluid passage in an ultrasonic surgical probe wherein the presence of bubbles in the irrigating fluid supplied to the needle is substantially reduced.

It is still another object of the present invention to provide an improved bubble control device which is readily positioned in an ultrasonic surgical tool construction which provides for improved reduction in the amount of bubbles in the irrigating fluid supplied to the needle and exiting from the fluid passage surrounding the needle to the surgical site.

These and other objects and advantages of the present invention will be apparent from the following description considered in conjunction with the accompanying drawings.

In accordance with the present invention an improved bubble control device is provided for an ultrasonic surgical probe or tool having a needle and a sleeve surrounding and spaced from the needle for at least a portion of the length of the needle.

More particularly, the ultrasonic surgical probe or tool with which the bubble control device of the present invention is particularly adapted to be used may comprise a handpiece having a body, a hollow elongated operating needle extending from one end of the body to an operating end, an ultrasonic motor capable of generating ultrasonic vibrations, means for coupling the needle to the ultrasonic motor, and a sleeve positioned about and spaced from the needle for at least a portion of the length of the needle, the annular space between the needle and the sleeve forming an annular passage to which fluid is supplied. The handpiece also includes means for connecting the handpiece to a source of suction, means for connecting the handpiece to a source of irrigating fluid and means on the first end of the body for securing the sleeve to the body. The handpiece includes a hollow bore, including a bore through or about the ultrasonic motor, coupled to the means for connecting the source of suction such that suction for aspiration is coupled to the hollow bore of the needle for aspirating material from the surgical site through the needle and handpiece. The body of the handpiece includes a passage coupling the means connecting the handpiece to a source of irrigating fluid to the annular passage between the needle and the sleeve.

The improved bubble control device of the present invention comprises a cylindrical hollow body having a bore defined therein and adapted to be positioned in the annular passage between the needle and the sleeve with the needle being received in the bore of the body. The bore defined by the body of the device has a first portion of greater diameter at one end and extends axially for more than half the length of the body and forms a cavity about a needle received in the bore of the body. The cavity formed by the first portion of the body is adapted to receive fluid supplied to the passage. The bore defined by the body of the device tapers to a second portion of lesser diameter, which lesser diameter is greater than the outside diameter of the needle. The second portion of the bore of the body extends to the opposite end of the body. The body further has at least one groove formed on its peripheral surface which extends from one end of the body to the other. Fluid supplied to the annular passage between the needle and the sleeve is restricted in its passage by being forced through the space between the at least one groove formed on the peripheral surface of the body and the sleeve, and through the space between said second portion of the body and the needle, thereby reducing the passage of bubbles formed in the fluid.

The improved bubble control device of the present invention preferably has a plurality of spaced apart grooves formed on the peripheral surface of the body and extending from one end of the body to the other. In this manner fluid supplied to the annular passage between the needle and the sleeve is restricted in its passage by being forced through the space between said plurality of grooves formed on the peripheral surface of the cylindrical body and the sleeve, and through the space between said second portion of the body and the needle, thereby reducing the passage of bubbles formed in the fluid.

Unexpectedly, it has been found that through the use of the bubble control device of the present invention considerably greater reduction in the amount of bubbles in the irrigating fluid passing from the ultrasonic transducer to the portion of the needle extending beyond the bubble control device than with bubble reducing devices previously known.

BRIEF DESCRIPTION OF THE DRAWINGS

FIG. 1 is a side view of a handpiece of an ultrasonic surgical probe having a bubble control device of the present invention installed therein.

FIG. 2 is an enlarged view of a portion of FIG. 1, partially in cross-section, showing the bubble control device of the present invention.

FIG. 3 is enlarged end view of the bubble control device of the invention, taken from the end of the device having the bore of lesser diameter.

FIG. 4 is a cross-sectional view taken along line 4—4 in FIG. 3.

DESCRIPTION OF THE PREFERRED EMBODIMENT

In the preferred embodiment of the present invention, the bubble control device of the invention, best shown generally by reference numeral 10 in FIGS. 2–4, is installed in a handpiece 12 of an ultrasonic surgical tool or probe, as will be hereinafter described.

Handpiece 12 includes a body 14, preferably of a nonconducting material, such as a polymer, enclosing an ultrasonic transducer or motor 16 capable of generating ultrasonic vibrations. Motor 16 is mounted within body 14 to provide an air space, designated by reference numeral 18, between motor 14 and the body 14. Extending from one end of motor 14 and integral therewith is a tubular extension or horn 20, which is within body 14, and which has a length which is critical and which is, in large part, determinative of the resonant frequency, as is known in the art. In the preferred embodiment, motor 14 and horn 20 have an aligned axial bore 22 which is coupled to connector 24, which is adapted to be connected to a source of suction (not shown). The end portion 26 of horn 20 opposite motor 14 is internally threaded to receive a hollow elongated operating needle 28 which has a first end portion 30 having a hexagonal portion 32 and an externally threaded end 34 which is received in the internally threaded portion 26 of horn 20 for securing needle 28 to horn 20. Power and control of the motor 16 is provided by means of power cord 38 which is connected to the motor and to a control unit (not shown) as known to the art.

Operating needle 28 is desirably tapered and its operating end 36 may be perpendicular to its axis or may be slanted as shown, or may have other shapes depending upon the surgical procedure to be performed as known to the art. Needle 28 is formed with a central bore 40 which communicates with bore 22 through motor 16 and horn 20 and with connector 24 to provide aspiration to the operating end 36 of the needle.

Body 14 of handpiece 12 has a substantially conical end 42 which encloses end portion 26 of horn 20, and has external threads 44 to which is releasably secured a sleeve 46 by means of internal threads 48 formed in an enlarged cap end 50 of the sleeve. Sleeve 46 is generally concentrically positioned about and spaced from needle 28. Sleeve 46 may be a single molded piece as shown, or may comprise two or more sections glued or otherwise secured together, with the several sections of polymers of different properties, e.g. one part relatively rigid and another part relatively flexible. Body 14 further includes an irrigating fluid passage 52 formed therein, and a nipple 54 located near the rear end of body 14 to which a supply of fluid (not shown) can be connected. Irrigating fluid passage 52 extends from communication with nipple 54 to substantially conical end 42 of body 14 and surrounds horn 20. Cap end 50 of sleeve 46 has a substantially cylindrical portion 56 extending beyond the end of horn 20 and beyond first end portion 30 of needle 28 and its hexagonal portion 32, forming a cavity 58, and tapers to a narrower portion 60, and then to a still narrower and tapered portion 62 which is annularly spaced from needle 28 forming an annular passage 64 therebetween, and extends to an open end 66 spaced from operating end 36 of needle 28. As shown in the drawing, irrigating fluid supplied to nipple 54 flows through passage 52, into cavity 58 between horn 20 and end of needle 28, into annular passage 64 and exits from the open end 66 of the sleeve.

The bubble control device 10 of the present invention, in this embodiment, has a generally cylindrical body 68 having an axial bore 70 therethrough. Bore 70 of device 10 has a first portion 72 having a diameter which is greater than the diameter of the remainder of bore 70 and extends axially for more than half of the length of body 68. Bore 70 in body 68 tapers inwardly in a second portion 74 of lesser diameter than that of first portion 72 extending to the opposite end of body 68, which at its narrowest diameter is greater than the diameter of needle 28. Second portion 74 of body 68 may taper to an annular shoulder 76 forming a narrow annular space between needle 28 and shoulder 76, as shown. First portion 72 of the bore of body 68 and shoulder 76 forms a cavity 78, which is adapted to receive needle 28 therethrough and at least partially surround first end portion 30 and hexagonal portion 32 of needle 28 received in cavity 78. Body 68 is adapted to be freely retained within the enlarged end portion 50 of sleeve 46. Body 68 has at least one groove 80 formed on the peripheral surface of the body extending from one end of body 68 to the other. Preferably body 68 has a plurality of grooves 80 formed on the peripheral surface, each spaced from the other and extending from one end of the body to the other. Most preferably, body 68 has four equidistantly spaced, parallel grooves formed on the peripheral surface of the body.

In the arrangement described above, cavitation bubbles formed in the irrigating fluid supplied to the annular passage 52 between needle 28 and sleeve 46 by contact with horn 20 and the first end portion 30 and hexagonal portion 32 of needle 28, due to the vibrations of those components, are restricted in their passage by being forced through the at least one groove 80 or the plurality of grooves 80 formed on the peripheral surface of body 68 and through the annular space between second portion 74 of the bore of body 68, and shoulder 76 and needle 28. In this manner, the passage of bubbles formed in the fluid is substantially reduced when passing to the annular passage 64 between needle 28 and sleeve 46. The reduction in the bubbles has been found to be substantially greater than obtained with previously known bubble control devices.

While a particular embodiment of the bubble control device of the invention has been shown and described, it will be appreciated by those skilled in the art that changes and modifications may be made thereto without departing from the invention in its broader aspects and as set forth in the following claims.

What is claimed is:

1. A bubble control device for an ultrasonic surgical probe having a needle and a sleeve spaced from the needle for at least a portion of the length of the needle and between which is an annular passage to which fluid is supplied, said device comprising a cylindrical hollow body having a bore defined therein and adapted to be positioned in the annular passage between the needle and the sleeve with the needle being received in said bore, said bore defined by said body having a first portion of greater diameter at one end and extending axially for more than half the length of the body and forming a cavity about the needle which is adapted to receive fluid supplied to the passage, said bore defined by said body tapering to a second portion of lesser diameter, which lesser diameter is greater than the outside diameter of the needle, said second portion extending to the opposite end of the body, and said body having at least one groove formed on the peripheral surface thereof extending from one end of the body to the other, whereby fluid supplied to the annular passage between the needle and the sleeve is restricted in its passage by being forced through said at least one groove formed on the peripheral surface of the body and through the space between said second portion of the body and the needle, thereby reducing the passage of bubbles formed in the fluid.

2. The device of claim 1 for an ultrasonic surgical probe having a needle connected to a transducer for causing the needle to ultrasonically vibrate and a sleeve having an enlarged end portion placed about and spaced from the connection of the needle and the transducer with the sleeve spaced from the needle for at least a portion of the length of the needle and between which is an annular passage to which fluid is supplied, said device being adapted to be freely retained within the enlarged end portion of the sleeve and at least partially surrounding the connection of the needle and the transducer with the connection being received in said cavity.

3. The device of claim 1 having a plurality of spaced apart grooves formed on the peripheral surface of the body and extending from one end of the body to the other, whereby fluid supplied to the annular passage between the needle and the sleeve is restricted in its passage by being forced through said plurality of grooves formed on the peripheral surface of the body and through the space between said second portion of the body and the needle, thereby reducing the passage of bubbles formed in the fluid.

4. The device of claim 3, wherein the plurality of spaced apart grooves comprises a pair of spaced apart grooves formed on the peripheral surface of said body and extending from one end of the body to the other.

5. The device of claim 3, wherein the plurality of spaced apart grooves comprises three spaced apart grooves formed on the peripheral surface of said body and extending from one end of the body to the other.

6. The device of claim 3, wherein the plurality of spaced apart grooves comprises four spaced apart grooves formed on the peripheral surface of said body and extending from one end of the body to the other.

7. The device of claim 6, wherein the spaced apart grooves are equidistantly spaced from each other.

8. A bubble control device for an ultrasonic surgical probe having a needle connected to a transducer for causing the needle to ultrasonically vibrate and a sleeve having an enlarged end portion placed about and spaced from the connection of the needle and the transducer with the sleeve spaced from the needle for at least a portion of the length of the sleeve and between which is an annular passage to which fluid is supplied, said device comprising a cylindrical hollow body having a bore defined therein and adapted to be positioned in the annular passage between the needle and the sleeve with the needle being received in said bore, said bore defined by said body having a first portion of greater diameter at one end and extending axially for more than half the length of the body and forming a cavity about the needle which is adapted to receive fluid supplied to the passage, said device further adapted to be freely retained within the enlarged end portion of the sleeve and at least partially surrounding the connection of the needle and the transducer with the connection being received in said cavity, said bore defined by said body tapering to a second portion of lesser diameter, which lesser diameter is greater than the outside diameter of the needle, said second portion extending to the opposite end of the body, and said body having a plurality of grooves formed on the peripheral surface thereof extending from one end of the body to the other, whereby fluid supplied to the annular passage between the needle and the sleeve is restricted in its passage by being forced through said plurality of grooves formed on the peripheral surface of the body and through the space between said second portion of the body and the needle, thereby reducing the passage of bubbles formed in the fluid.

9. The device of claim 8, wherein the plurality of spaced apart grooves comprises a pair of spaced apart grooves formed on the peripheral surface of said body and extending from one end of the body to the other.

10. The device of claim 8, wherein the plurality of spaced apart grooves comprises three spaced apart grooves formed on the peripheral surface of said body and extending from one end of the body to the other.

11. The device of claim 8, wherein the plurality of spaced apart grooves comprises four spaced apart grooves formed on the peripheral surface of said body and extending from one end of the body to the other.

12. The device of claim 11, wherein the spaced apart grooves are equidistantly spaced from each other.

13. An ultrasonic surgical probe handpiece comprising:

a. a handpiece body;

b. a hollow elongated operating needle extending from a first end thereof to an operating end;

c. an ultrasonic motor capable of generating ultrasonic vibrations contained therein;

d. means for connecting the handpiece and needle to a source of suction, e. means on the first end of said body for coupling the needle to the ultrasonic motor for receiving and transmitting ultrasonic vibrations from the motor along the length of the needle to the operating end;

f. a sleeve having an enlarged end portion placed about and spaced from the means coupling the needle to the ultrasonic motor with the sleeve spaced from the needle for at least a portion of the length of the sleeve and between which is an annular passage to which fluid is supplied;

g. means on the first end of said body for securing the sleeve to the body; and h. a cylindrical hollow body having a bore defined therein, said bore defined by said body having a first portion of greater diameter at one end and extending axially for more than half the length of the body and forming a cavity about the needle which is adapted to receive fluid supplied to the passage, said bore defined by said body tapering to a second portion of lesser diameter, which lesser diameter is greater than the outside diameter of the needle, said second portion extending to the opposite end of the body, said body being adapted to be freely retained within the enlarged end portion of the sleeve and at least partially surrounding the means coupling the needle to the ultrasonic motor with the means being received in said cavity with the needle being received in said bore, and said body having at least one groove formed on the peripheral surface thereof extending from one end of the body to the other, whereby fluid supplied to the annular passage between the needle and the sleeve is restricted in its passage by being forced through said at least one groove formed on the peripheral surface of the body and through the space between said second portion of the body and the needle, thereby reducing the passage of bubbles formed in the fluid.

14. The handpiece of claim 13 wherein the cylindrical body has a plurality of spaced apart grooves formed on the peripheral surface of the body and extending from one end of the body to the other, whereby fluid supplied to the annular passage between the needle and the sleeve is restricted in its passage by being forced through said plurality of grooves formed on the peripheral surface of the cylindrical body and through the space between said second portion of the body and the needle, thereby reducing the passage of bubbles formed in the fluid.

15. The handpiece of claim 14, wherein the plurality of spaced apart grooves formed on the peripheral surface of the cylindrical body comprises a pair of spaced apart grooves formed on the peripheral surface of said body, each extending from one end of the body to the other.

16. The handpiece of claim 14, wherein the plurality of spaced apart grooves formed on the peripheral surface of the cylindrical body comprises three spaced apart grooves formed on the peripheral surface of said body, each extending from one end of the body to the other.

17. The handpiece of claim 14, wherein the plurality of spaced apart grooves formed on the peripheral surface of the cylindrical body comprises four spaced apart grooves formed on the peripheral surface of said body, each extending from one end of the body to the other.

18. The handpiece of claim 17, wherein the spaced apart grooves formed on the peripheral surface of the cylindrical body are equidistantly spaced from each other.

* * * * *